(12) United States Patent
Mahfouz et al.

(10) Patent No.: US 8,444,564 B2
(45) Date of Patent: May 21, 2013

(54) NONINVASIVE DIAGNOSTIC SYSTEM

(75) Inventors: Mohamed M. Mahfouz, Knoxville, TN (US); Rick Komistek, Knoxville, TN (US); Ray C. Wasielewski, New Albany, OH (US)

(73) Assignee: JointVue, LLC, Columbus, OH (US)

( * ) Notice: Subject to any disclaimer, the term of this patent is extended or adjusted under 35 U.S.C. 154(b) by 662 days.

(21) Appl. No.: 12/364,267

(22) Filed: Feb. 2, 2009

(65) Prior Publication Data
US 2010/0198067 A1 Aug. 5, 2010

(51) Int. Cl.
*A61B 8/00* (2006.01)
(52) U.S. Cl.
USPC ............ 600/449; 600/437; 600/595; 600/407
(58) Field of Classification Search
USPC .......................................... 600/437, 449, 595
See application file for complete search history.

(56) References Cited

U.S. PATENT DOCUMENTS

| | | | |
|---|---|---|---|
| 3,881,164 A * | 4/1975 | Kossoff | 367/138 |
| 4,476,873 A | 10/1984 | Sorenson et al. | |
| 5,394,875 A | 3/1995 | Lewis et al. | |
| 5,413,116 A * | 5/1995 | Radke et al. | 600/590 |
| 5,447,154 A * | 9/1995 | Cinquin et al. | 600/429 |
| 5,488,952 A | 2/1996 | Schoolman | |
| 5,771,310 A | 6/1998 | Vannah | |
| 5,806,521 A | 9/1998 | Morimoto et al. | |
| 6,106,464 A | 8/2000 | Bass et al. | |
| 6,120,453 A | 9/2000 | Sharp | |
| 6,190,320 B1 | 2/2001 | Lelong | |
| 6,280,387 B1 | 8/2001 | Deforge et al. | |
| 6,537,233 B1 | 3/2003 | Rangayyan et al. | |
| 6,569,098 B2 | 5/2003 | Kawchuk | |
| 6,585,651 B2 | 7/2003 | Nolte et al. | |
| 7,454,242 B2 | 11/2008 | Fear et al. | |

(Continued)

FOREIGN PATENT DOCUMENTS

| | | |
|---|---|---|
| WO | 0063719 A1 | 10/2000 |
| WO | PCT/US2010/022939 | 3/2010 |
| WO | WO 2010/088696 A1 | 8/2010 |

OTHER PUBLICATIONS

United States Patent and Trademark Office, "International Preliminary Report on Patentability," in corresponding International Application No. PCT/US2010/022939, mailed Aug. 2, 2011, 7 pp.

(Continued)

*Primary Examiner* — Long V. Le
*Assistant Examiner* — Farshad Negarestan
(74) *Attorney, Agent, or Firm* — Wood, Herron & Evans, LLP

(57) ABSTRACT

A method for diagnosing a joint condition includes in one embodiment: creating a 3d model of the patient specific bone; registering the patient's bone with the bone model; tracking the motion of the patient specific bone through a range of motion; selecting a database including empirical mathematical descriptions of the motion of a plurality actual bones through ranges of motion; and comparing the motion of the patient specific bone to the database.

15 Claims, 16 Drawing Sheets

U.S. PATENT DOCUMENTS

| | | | |
|---|---|---|---|
| 2004/0152970 | A1 | 8/2004 | Hunter et al. |
| 2005/0111718 | A1 | 5/2005 | MacMahon et al. |
| 2007/0249967 | A1* | 10/2007 | Buly et al. .................. 600/595 |
| 2007/0282200 | A1 | 12/2007 | Johnson et al. |
| 2007/0287900 | A1* | 12/2007 | Breen et al. .................. 600/407 |
| 2008/0025463 | A1 | 1/2008 | Lang |
| 2008/0094396 | A1 | 4/2008 | Sabczynsdi et al. |
| 2008/0114270 | A1 | 5/2008 | DiSilvestro et al. |
| 2009/0015832 | A1 | 1/2009 | Popovic et al. |

OTHER PUBLICATIONS

European Patent Office, "International Search Report and Written Opinion," in corresponding International Application No. PCT/US2011/046318, mailed Nov. 11, 2011, 13 pp.

United States Patent and Trademark Office, "International Search Report and Written Opinion," in corresponding International Application No. PCT/US20111054952, mailed Jan. 26, 2012, 9 pp.

* cited by examiner

NONINVASIVE DIAGNOSTIC SYSTEM

FIELD OF THE INVENTION

The present invention relates to diagnosis of bodily abnormalities, and more particularly, to devices and methods for evaluating the physiological condition of bodily tissue to discern whether abnormalities exist and the extent of any abnormalities. While the exemplary embodiments disclosed herein are utilized and discussed with respect to a human knee joint, it is to be understood that other joints and bodily tissues may be likewise diagnosed.

BACKGROUND OF THE INVENTION

In humans, the knee joint is functionally controlled by a mechanical system governed by three unique types of forces: (1) active forces resulting in motion, such as those resulting from muscle flexing or relaxing; (2) constraining forces that constrain motion, such as those resulting from ligaments being in tension; and (3) compressive forces that resist motion, such as those acting upon bones. In addition to the foregoing bodily tissues accounting for these three forces, cartilage and meniscus also produce a dampening effect dissipating the compressive forces propagating to other joints Knee joint motions are stabilized primarily by four ligaments, which restrict and regulate the relative motion between the femur, tibia, and patella. These ligaments are the anterior cruciate ligament (ACL), the posterior cruciate ligament (PCL), the medial collateral ligament (MCL), and the lateral collateral ligament (LCL), as shown in FIGS. 1 and 2. An injury to any of these ligaments or other soft-tissue structures can cause detectable changes in knee kinematics and the creation of detectable patterns of vibration representative of the type of knee joint injury and the severity of the injury. These visual and auditory changes are produced by the bones while moving in a distorted kinematic pattern, and they differ significantly from the look and vibration of a properly balanced knee joint moving through a range of motion.

Many research studies have been conducted to assess knee vibration and correlate it with clinical data regarding various joint problems using microphones with or without stethoscope equipment. However, it has been shown that microphones cannot reliably detect joint frequencies, especially those experiencing strong interference from noise, and the signal clearance can substantially influenced by skin friction. It has been hypothesized that the failure associated with the interpretation of sound emissions and possible reasons for occurrence is directly attributable to the complicity of the sound signal, the unknown noise factors, and unknown sound center. It is desirable, therefore, to provide a diagnostic tool that compares patient specific data with kinematic data by providing visual feedback to clinicians.

SUMMARY OF THE INVENTION

The present invention, in one embodiment, provides a patient specific 3D model of a patient's joint, including bone and soft tissue. This model is then registered to the patient's actual bone so that as the joint is taken through a range of motion it can be visualized on a computer screen. A physician can then use the computer generated image to make a diagnosis or compare the motion of the actual bone to a database of clinically relevant information on desirable or undesirable joint motion.

The exemplary embodiments of the present invention include a diagnostic system for mammalian bodies to determine the type of injury and extent of injury using kinematic data and/or vibration data. In particular, an exemplary method and embodiment are directed to a knee joint diagnostic system for automatically determining the type of injury and the extent to which ligaments, muscles, bones, meniscus, and cartilage may be affected by an injury through analyzing the kinematics of the knee joint, while also analyzing the pattern and special distribution of the vibration produced knee joint movement. An exemplary process flow diagram for this exemplary method is shown in FIG. 3.

To evaluate knee kinematics, patient-specific 3D models of the distal femur, proximal tibia, and the patella are constructed using pulse echo A-mode ultrasound based 3D model reconstruction technology. In addition, patient-specific kinematic data is obtained for the motions of the femur, tibia, and patella using pulse A-mode ultrasound. Finally, patient specific vibration data is obtained while the knee joint is taken through a range of motion and loaded in real-world conditions. In exemplary form, the vibration data and kinematic data are taken at the same time using the single data acquisition device. In a further exemplary embodiment, if the data is acquired in a physician's office, the data is displayed in real-time on a split screen monitor. If, however, the data is acquired outside of the doctor's office, a recording device and memory may be utilized to record the data in a time synched manner. In a yet a further exemplary embodiment, the patient may be given an actuator that is operative to note the general time frame within which the patient felt a particular pain or sever pain to allow a correlation between pain felt by the patient and the kinematics and vibration occurring at roughly the same time.

Patient-specific data is analyzed by a trained neural network in order to provide an automated output as to the existence of an injury, the type of injury, and the severity of the injury. This neural network may be accessible via the internet or may reside on a physician's local computer. In addition, or in the alternative, patient-specific data may be analyzed by a physician to make the diagnosis directly without the aid of the neural network.

Using the exemplary methods and devices as disclosed herein, a physician may diagnose a bodily injury without requiring experimental surgery or requiring exposure of the patient to radiation from still X-rays or fluoroscopy. In addition, the data taken regarding each patient is continuous through a range of motion, in contrast to X-rays and fluoroscopy which take images at distinct points with significant range of motion gaps. In addition, data taken in accordance with the exemplary method and devices disclosed herein also contrasts data taken by a magnetic resonance imaging machine, not only because the data taken is continuous along the range of motion, but also because the bodily portion evaluated is acting under loaded conditions in a dynamic environment.

It is an object of the present invention to provide a method of creating a three dimensional model of a patient's bone using tracked pulse-echo A-Mode ultrasound and atlas-based deformable models.

It is another object of the present invention to provide a method of registering a patient's bone with a three dimensional model of the patient's actual bone.

Another object of the present invention is to provide a method of tracking the motion of a patient's actual bone through space and showing the same on a computer screen.

Yet another object of the present invention is to provide method of tracking at lest two bones relative to one another as three dimensional models on a computer screen as the actual bones are taken through a range of motion.

It is also an object of the present invention to provide a method of diagnosis for joint conditions based on a database of kinematic or other information about joint motion.

DETAILED DESCRIPTION

The exemplary embodiments of the present invention are described and illustrated below to encompass diagnosis of bodily abnormalities and, more particularly, devices and methods for evaluating the physiological condition of bodily tissue to discern whether abnormalities exist and the next of any abnormalities. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods and features that one of ordinary skill should recognize as not being a requisite to fall within the scope of the present invention. In exemplary fashion, the embodiments disclosed herein are described with respect to diagnosing a knee joint injury. Nevertheless, the embodiments may be utilized to diagnose other joints and bodily tissue injuries, as the knee joint is merely exemplary to facilitate an understanding of the embodiments disclosed.

Figure 1:
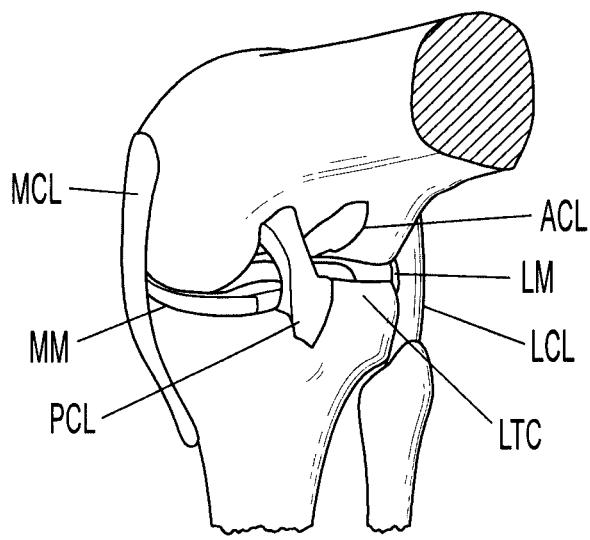
FIG. 1 is a posterior view of a human knee joint in a fixed position.
Figure 2:
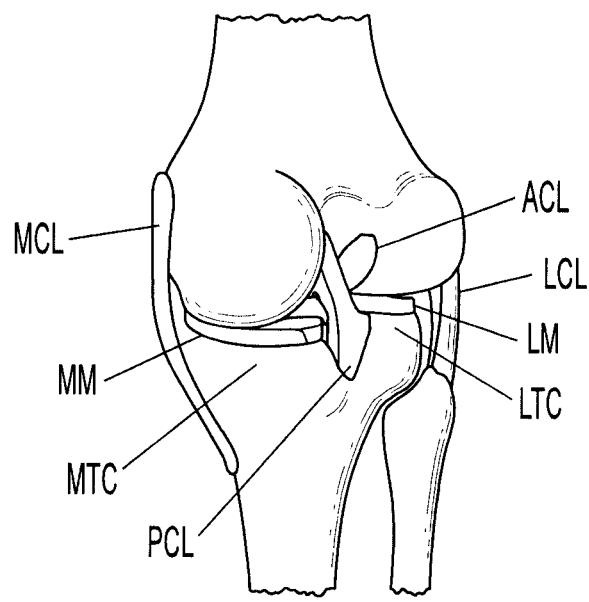
FIG. 2 is a posterior view of a human knee joint in an extended position.
Figure 3:
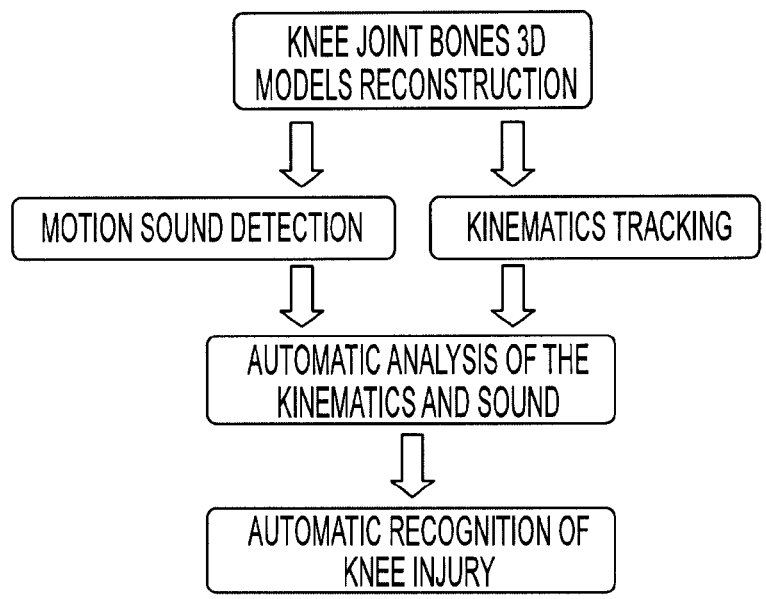
FIG. 3 is an exemplary process flow diagram using exemplary methods within the scope of the present invention.
Figure 4:
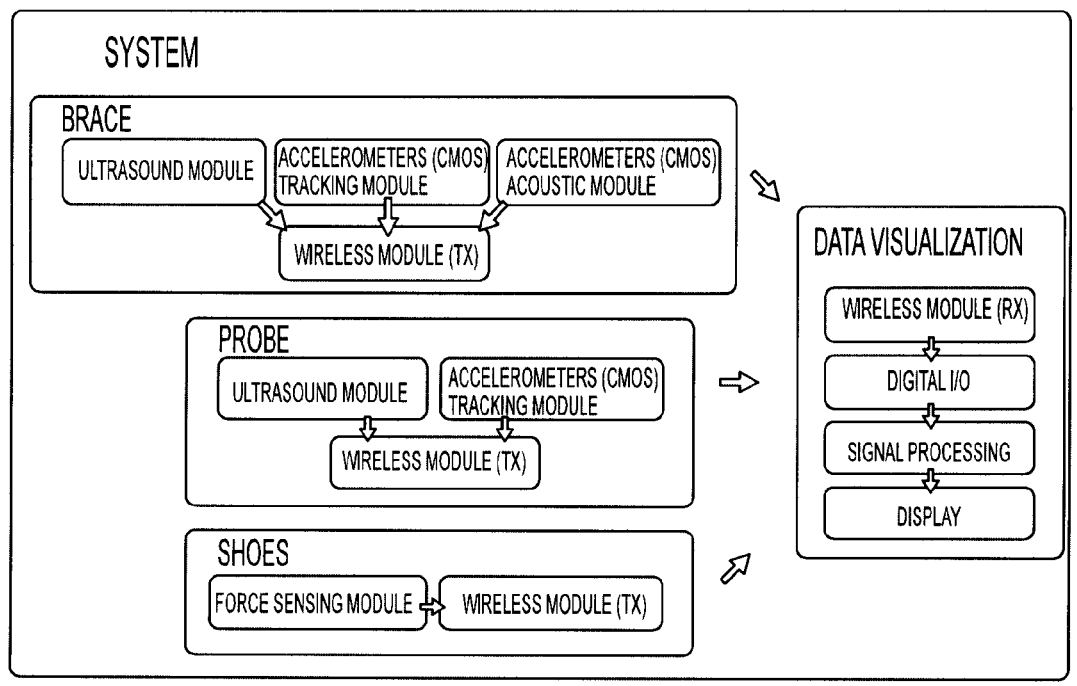
FIG. 4 is a schematic diagram of the modules of an exemplary diagnostic system.

Referencing FIG. 4, a first exemplary diagnostic system includes four modules: (1) a pulse echo A-mode ultrasound based 3D model reconstruction (PEAUMR) module for constructing 3D patient specific models of the knee joint bones; (2) a joint kinematics tracking (JKT) module for tracking kinematics of the knee joint using the patient-specific 3D model of the knee joint from the PEAUMR module; (3) a vibration detection (VD) module for capturing sounds emanating from the knee joint while in motion; and (4) an intelligent diagnosis (ID) module for identifying pathological cases of the knee joint using kinematic data and associated vibration data gathered during the joint motion. Each of these four modules is described in further detail in the following sections. The foot sensor interacts in real time with these other modules providing dynamic force data.

It will be understood by those of skill in the art that the system described above is usable with or without the use of the vibration detection module. For example, one may use the present invention by mathematically describing the relative motion of bones in a patient's joint as such motion is tracked in a 3D patient specific bone model and comparing such description with a database of mathematical descriptions of joint motion. The database could contain mathematical descriptions of healthy or clinically undesirable joint motion.

Figure 5:
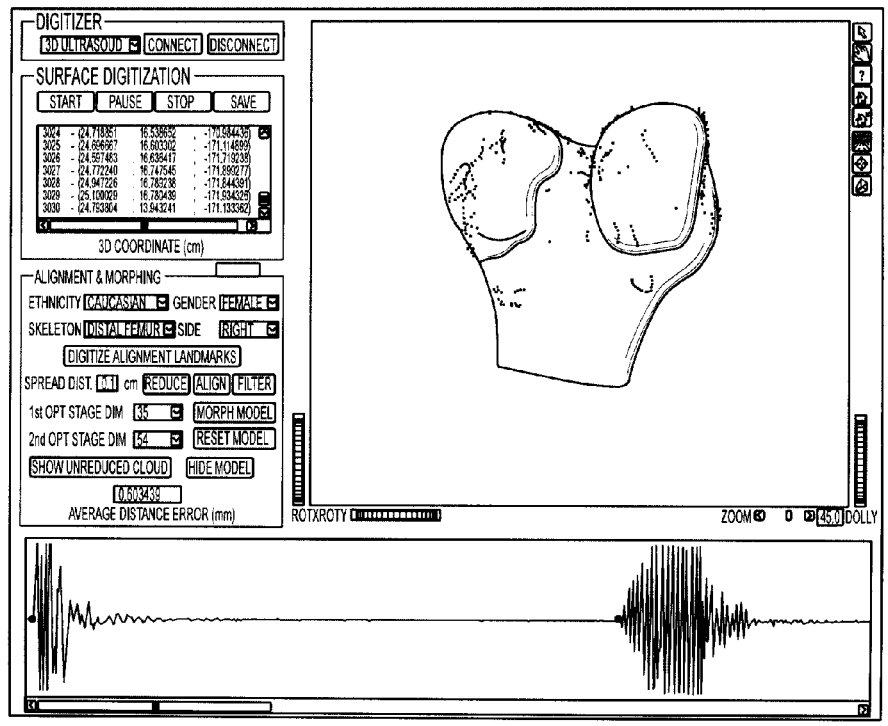
FIG. 5 is a screen shot of a software user interface for bone modeling.

Referring to FIG. 5, the PEAUMR module constructs a 3D model of a subject's (e.g., a patient) bones by transcutaneously acquiring a set of 3D data points that in total are representative of the shape of the bone's surface using a tracked pulse echo A-mode ultrasound probe. The probe consists of a single ultrasound transducer attached to a global localizer. The global localizer may be optical, inertial, electromagnetic or ultra wide band radio frequency. The probe is battery-powered and connected wirelessly to a computer in order to record the set points and construct a unique or patient-specific bone model using an atlas-based deformable model technique.

Figure 6:
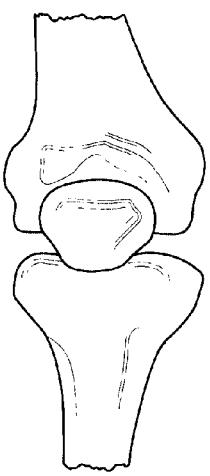
FIG. 6 is an anterior view of the bones of a human knee joint in an extended position.

The computer includes software that interprets data from the tracked pulse echo A-mode ultrasound probe and is operative to construct the 3D models of the patient's bones, which will look very similar to the model shown in FIG. 6. The patient-specific bone is reconstructed using the set of points collected from the bone's surface transcuateously by the tracked ultrasound probe. These points are then used by the atlas-based deformable model software to reconstruct the 3D model of the patient's bone.

In exemplary form, the software includes a plurality of bone models of the femur, tibia, and patella that are classified, for example, based upon ethnicity, gender, skeletal bone to be modeled, and the side of the body the bone is located. Each of these classifications is accounted for by the dropdown menus of the software so that the model initially chosen by the software most closely approximates the bode of the patient.

After the software selects the bone model to approximate the bone of the patient, the ultrasound transducer probe is repositioned on the exterior of the skin and data points are generated and applied to the model bone (in this case a distal femur), numerically recorded and viewable in a data window, and ultimately utilized by the software to conform the bone model to the patient's actual bone shape. Obviously, a higher number of data points imposed on the model will generally result in a more accurate patient model. Nevertheless, in view of the model bones already taking into account numerous traits of the patient (ethnicity, gender, bone modeled, and body side of the bone), it is quite possible to construct an accurate patient-specific 3D model with as few as 150 data points, which typically can be taken by repositioning the probe over the bone for 30 seconds for each bone. In this example, it is preferable for the data to be acquired both while the knee is bent and extended to more accurately shape the ends of the bones. This same procedure is repeated for the remaining bones of the joint, in this case the proximal end of the tibia and the patella, in order for the software to combine the bones thereby forming the joint. Ultrasound will not be affected whether the patient has normal or prosthetic implant. The 3D model of the femur can be resected and attached with the implanted CAD model.

Figure 7:
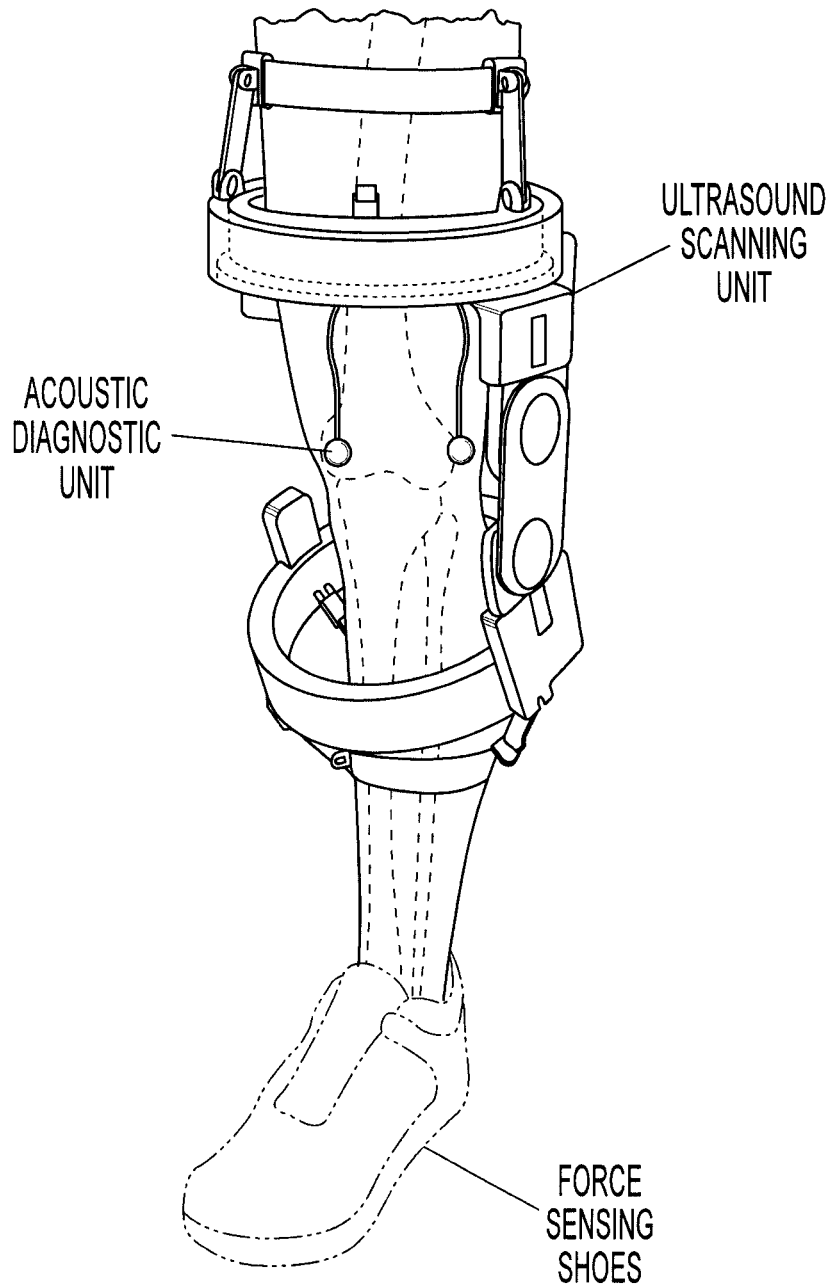
FIG. 7 is a pictorial representation of a human leg having an exemplary brace attached to a distal segment of the femur, and exemplary brace attached to a proximal segment of the tibia, a sensor mounted proximate the patella, and a foot pressure sensing shoe.

Referring to FIG. 7, the JKT module tracks the kinematics of the knee joint using the patient-specific 3D bone models from the PEAUMR module. In this exemplary embodiment, motion tracking of the patient's knee joint bones is performed using one or more bone motion tracking braces. In exemplary form, the bone motion tracking brace includes pulse echo A-mode ultrasound transducers to transcutaneously localize points on the bones surface. Incidentally, the pulse echo A-mode ultrasound transducers may or may not be identical to the pulse echo A-mode ultrasound transducers used by the PEAUMR module. Commercially available transducers for use with the exemplary embodiments include, without limitation, the Olympus immersion unfocused 3.5 MHz transducer. The force sensing shoe detects the ground reactive pressures simultaneous with knee joint kinematic data acquisition.

Each ultrasound transducer is tracked using an accelerometer or a sensor-specific localizer (or any other appropriate inertial sensor). The resulting localized bone points generated from the outputs of the ultrasound transducers are used in combination with the patient specific 3D bone models to discern bone movement while the knee joint is taken through a range of motion. In exemplary form, three braces and a foot force sensing shoe are used to track knee joint kinematics and dynamic forces: (a) a first brace is positioned proximate the distal portion of the femur; (b) a second brace is positioned proximate the distal end of the tibia; and, (c) a third brace is positioned proximate the patella region.

Figure 8:
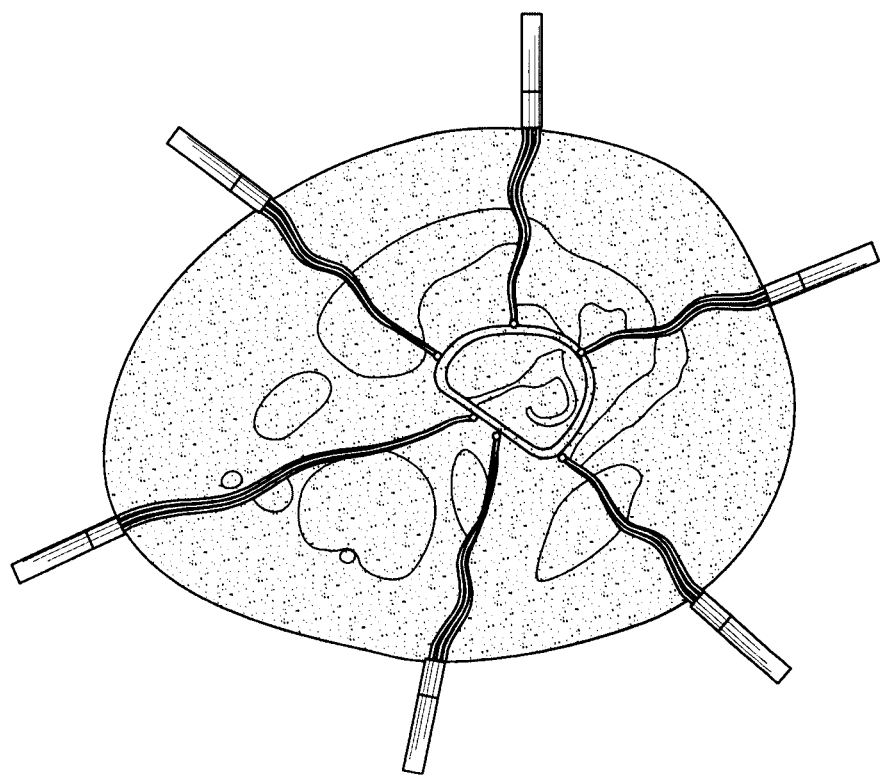
FIG. 8 is a is an illustration of a CT slice of the transcutaneous detection of a bone's surface using pulse echo A-mode ultrasound.

Referring to FIG. 8, an exemplary bone motion tacking brace includes a plurality of pulse echo A-mode ultrasound transducers for transcutaneous detection of the bone's surface and inertia-based localizers to track the motion of the ultrasound transducers, which in turn, track the bones motion. Each brace is wirelessly connected to a computer operative to perform computations and visualization in real-time showing movements of the patient-specific 3D bone models paralleling movements of the patient's actual knee joint in a time synchronized manner. Each exemplary brace include a rigid or semi-rigid body having a plurality (two or more) of complementary metal oxide semiconductor (CMOS) inertia-based sensors attached thereto. The position of each sensor and/or transducer is tracked by using the equation of motion: $F_r + F_r^* = 0$, where, $F_r$ is a summation of all the generalized active forces in the system, and $F_r^*$ is a summation of all the generalized inertia forces in the system. The homogenous transformation between the localizer's reference coordinate frame and the world coordinate frame is calculated using the positions of multiple inertia sensors. The following equation calculates the linear movement of the transducer: $v(n+1)=v(n)+a(n)dt$ and $s(n+1)=s(n)+v(n)dt-0.5a(n)dt2$, where $s(n+1)$ is position at the current state, $s(n)$ is the position from the previous state, $v(n+1)$ is instantaneous velocity of the current state, $v(n)$ is the velocity from previous state, and $a(n)$ is the acceleration from the accelerometer and dt is the sampling time interval. The previous equations describe the dynamic motion and positioning of a point in 3D Euclidean space. Additionally information is needed to describe a 3D body orientation and motion. The orientation of the transducer can be described by using a gravity based accelerometer (example: ADXL-330, analog device) by extracting the tilting information from each pair of orthogonal axis. The acceleration output on x, y, or z due to gravity is equal to the following: $Ai = (Vout_x - Voff)/S$, where Ai is the acceleration at x, y, or z axis, $Vout_i$ is the voltage output from the x, y, or z axis, Voff is the offset voltage, and S is the sensitivity of the accelerometer. The yaw, pitch and row can be calculated as shown in the following:

$$\rho = \arctan\left(\frac{Ax}{\sqrt{A_Y^2 + A_Z^2}}\right)$$

$$\phi = \arctan\left(\frac{Ay}{\sqrt{A_X^2 + A_Z^2}}\right)$$

$$\theta = \arctan\left(\frac{\sqrt{A_Y^2 + A_X^2}}{Az}\right)$$

where pitch is $\rho$, which is x-axis relative to the ground, roll is $\phi$, which is y-axis relative to the ground, and row is $\theta$, which is z-axis relative to the ground. Since the accelerometer is based using gravity, the orientation does not require information from the previous state once the sensor is calibrated. The static calibration requires the resultant sum of accelerations from the 3 axis equal to 1 g. Alternatively, an orientation sensor that gives yaw, pitch, and row information of the body are also commercially available (example: IDG-300, Invensense). The orientation of the transducer can then be resolved by using direction cosine matrix transformation:

$$\begin{bmatrix} X_2 \\ Y_2 \\ Z_2 \end{bmatrix} = \begin{bmatrix} C\theta C\phi & C\theta S\phi S\rho - S\theta C\rho & C\theta S\phi C\rho - S\theta S\rho \\ S\theta C\phi & S\theta S\phi S\rho - C\theta C\rho & S\theta S\phi C\rho - C\theta S\rho \\ -S\phi & C\phi S\rho & C\theta C\rho \end{bmatrix} \begin{bmatrix} X_1 \\ Y_1 \\ Z_1 \end{bmatrix}$$

where C shorts for cosine and S shorts for sine.

Figure 9:
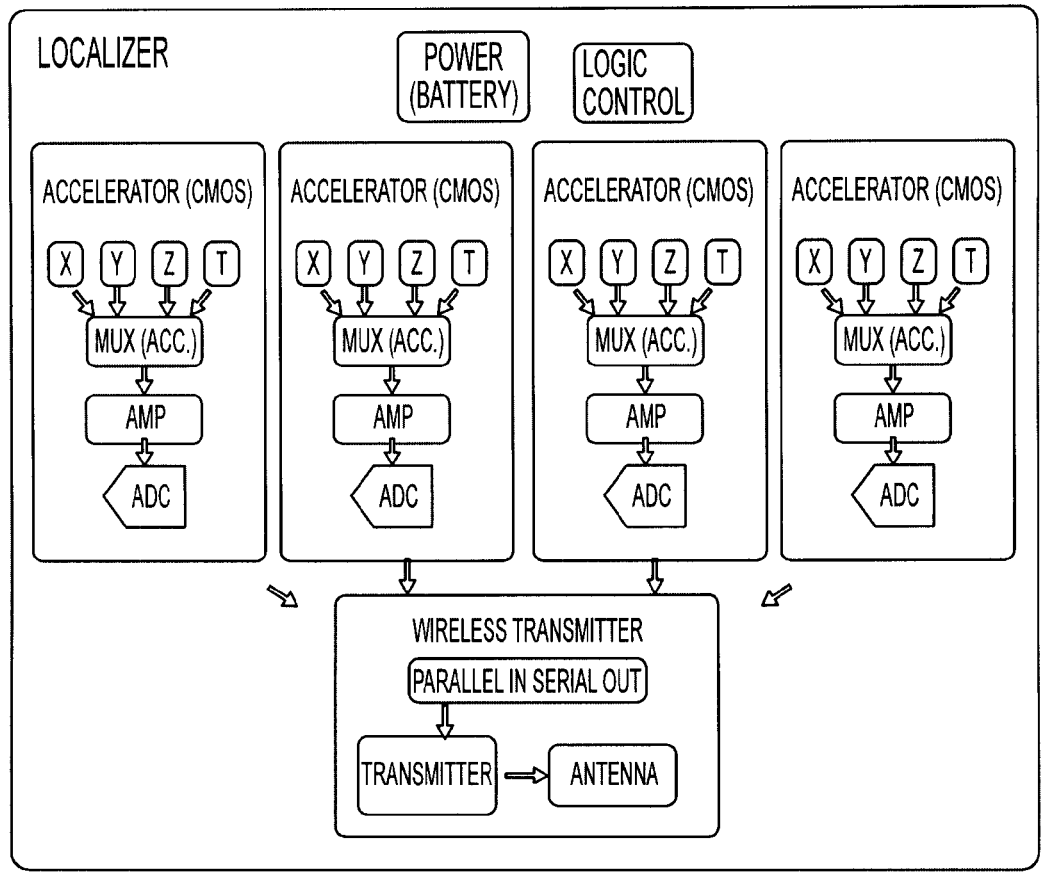
FIG. 9 is a schematic of an exemplary inertia-based localizer circuit.

Referring to FIG. 9, an accelerometer based localizer is used to track each pulse echo A-mode ultrasound transducer mounted to the brace. The localizer comprises a plurality of nodes, with each node comprising a CMOS accelerometer and a temperature sensor for thermal drift comparison. Each node is integrated to minimize noise and distortion. The outputs of the accelerometers regarding the X, Y, and Z coordinates and temperature sensor are directed to a multiplexer that multiplexes the signals. Multiplexed outputs are amplified by an amplifier and then directed to an analog-to-digital converter. The digital conversion of the signal can be performed within or outside the CMOS sensors chip. Outputted digital signals are directed to a wireless transmitter by way of a parallel input/serial output device.

Figure 10:
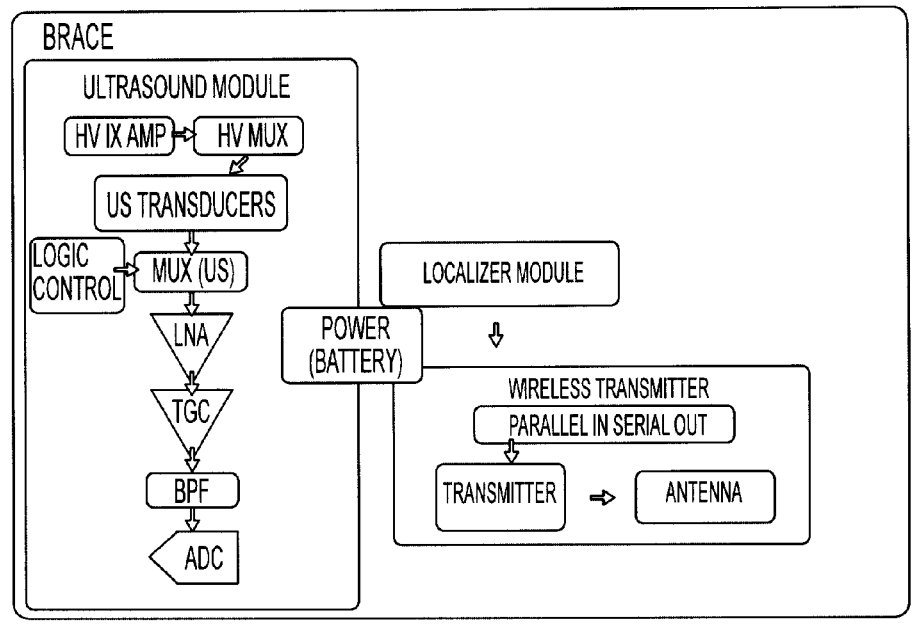
FIG. 10 is a schematic of an exemplary brace circuit architecture.

Referring to FIG. 10, each of the three exemplary design alternatives for the brace has a similar electronic architecture. An exemplary electronic architecture includes a high voltage amplifier circuit feeding a voltage multiplexer circuit to excite each ultrasound transducer and thereby acting as an analog switch. The echo signals from each transducer are multiplexed pursuant to a logic control directing the opening of the switches in the multiplexer circuit at precise intervals. An exemplary logic control is the MSP430 available from Texas Instruments. The output from the multiplexer circuit is amplified by an amplifier circuit, signal conditioned using a signal conditioning circuit, and digitized using an analog-to-digital converter. Electric power to the foregoing components is supplied by way of a battery, which also supplies power to a wireless transmitter module. In exemplary form, the wireless transmitter module utilizes the universe asynchronous receiver/transmitter (UART) protocol. The module includes a wireless transmitter circuit receiving the output of the first in-first out (FIFO) buffer of the analog-to-digital converter by way of a serial interface. An output from the wireless transmitter circuit is conveyed using a serial link coupled to an antenna. Signals conveyed through the antenna are broadcast for reception by a wireless receiver coupled to a controller computer.

Figure 11:
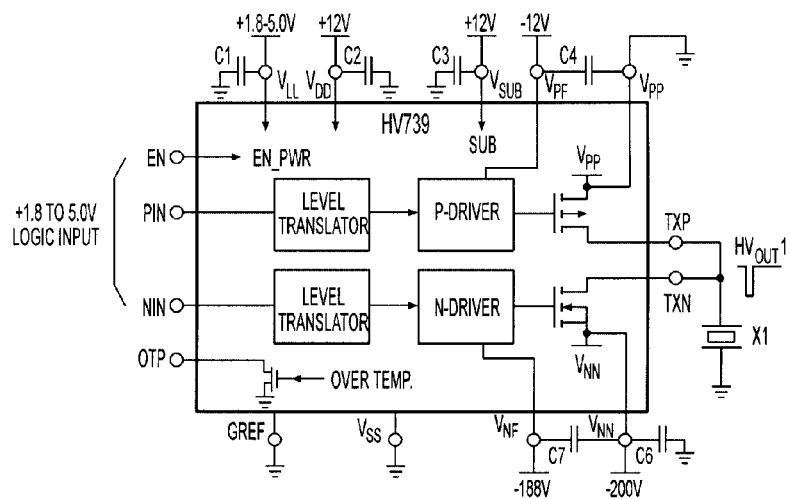
FIG. 11 is a circuit schematic of an exemplary high voltage amplifier.
Figure 12:
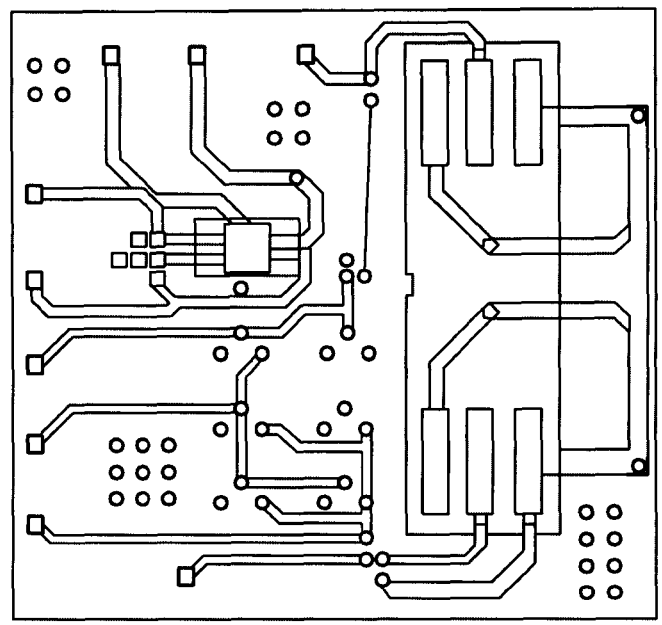
FIG. 12 is a circuit layout for the exemplary high voltage amplifier of FIG. 11.

Referring to FIGS. 11 and 12, an exemplary high voltage circuit is utilized to trigger and generate the excitation energy for the piezoelectric crystal in the transducer. Exemplary high voltage circuits for use in this embodiment include, without limitation, the pulsar integrated circuit (HV379) available from Supertex.

Figure 13:
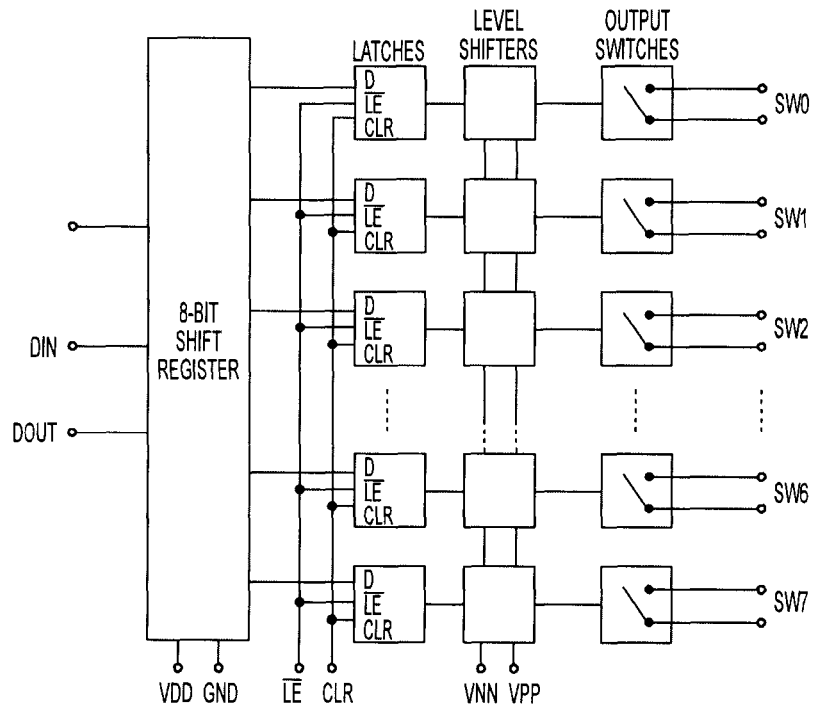
FIG. 13 is a block diagram for an exemplary high voltage multiplexer.

Referencing FIG. 13, an exemplary high voltage multiplexer is utilized to trigger and excite multiple piezoelectric transducers without increasing the number of high voltage circuit mentioned with regard to FIG. 11. Exemplary high voltage multiplexers for use in this embodiment include, without limitation, the high voltage multiplexer (HV2221) available from Supertex. The advantage of using a high voltage multiplexer is the ability to use CMOS level control circuitry, thereby making the control logic compatible with virtually any microcontroller or field programmable gate array commercially available.

Figure 14:
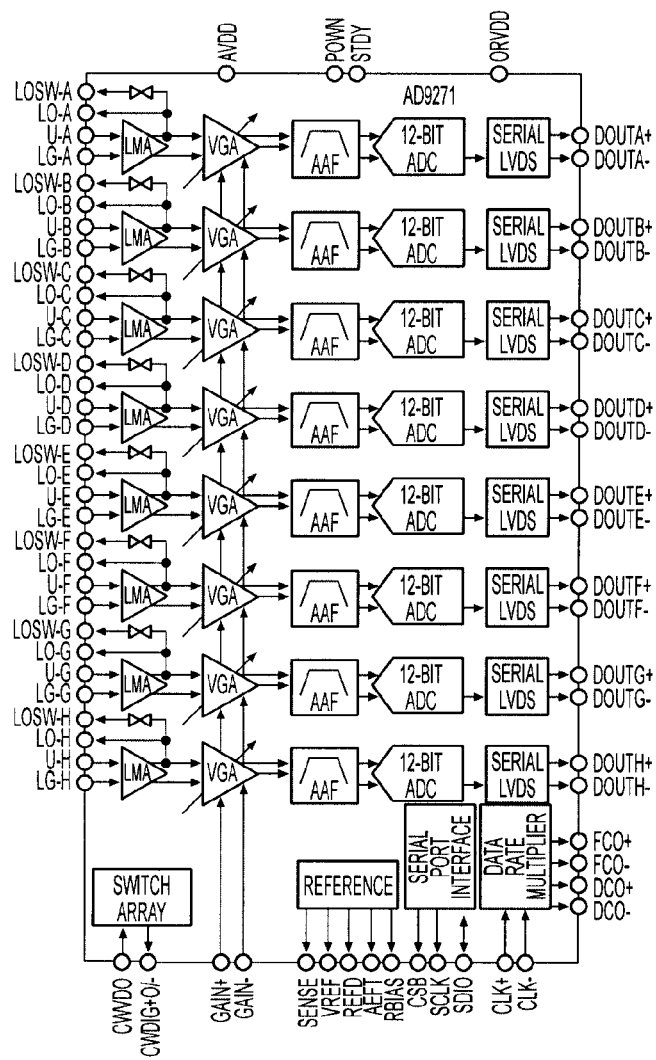
FIG. 14 is a block diagram for an exemplary receiving circuit.

Referring to FIG. 14, an exemplary receiving circuit, which comprises the multiplexer circuit, the amplifier circuit, the signal conditioning circuit, and the analog-to-digital converter, is utilized to receive the echo signals from each transducer. Exemplary receiving circuits for use in this embodiment include, without limitation, the AD9271 8-channel ultrasound receiving integrated circuit available from Analog Devices.

Figure 15:
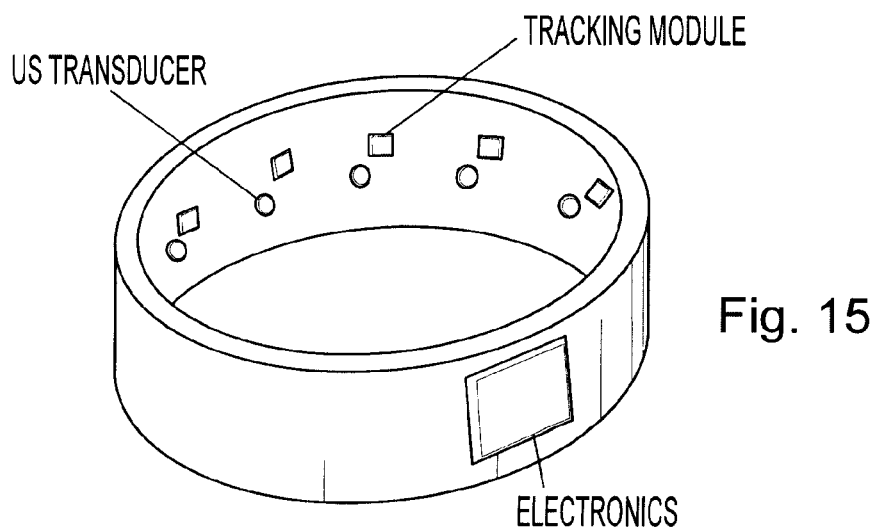
FIG. 15 is a pictorial representation of an exemplary kinematics tracking brace.

Referring to FIG. 15, a first exemplary bone tracking brace includes a plurality of transducers mounted thereto. Each transducer is responsible for determining the location of a point on the surface of the bone for each motion tracking frame. Problems of locating and tracking the bone using ultrasound data are reduced as the motion of the bone relative to the skin is small compared to the gross joint motion. There are at least three approaches disclosed herein for tracking the motion of the ultrasound transducers themselves. The first approach, commonly referred to herein as the ITT (Individual transducer tracking) approach, involves each transducer in the brace having an inertia-based localizer to individually track each transducer. Using the ITT approach, in exemplary form, the transducers are held together flexible length straps.

Figure 16:
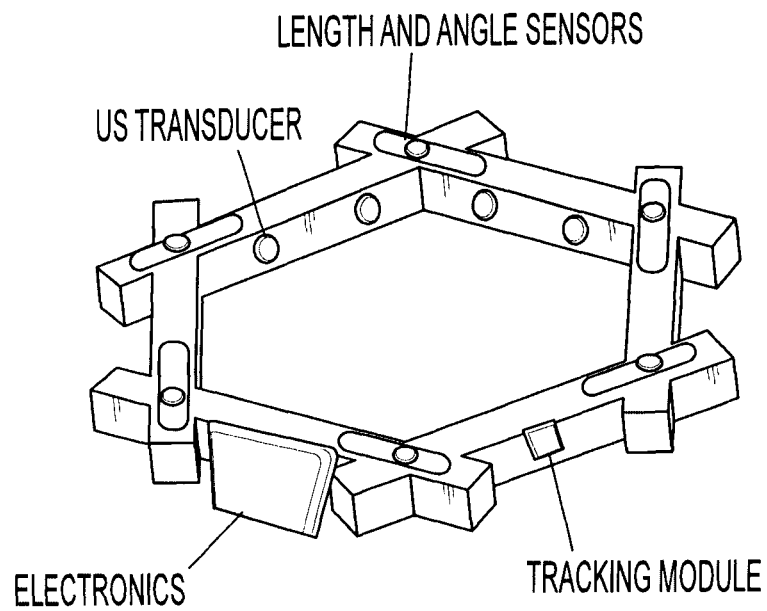
FIG. 16 is a pictorial representation of an alternative exemplary kinematics tracking brace.

Referencing FIG. 16, a second approach, commonly referred to herein as the ITML (Inter-transducers Mechanical Links) approach, involves the transducers being connected to each other by movable mechanical links. Each mechanical link includes length and angle sensors that allow for detection of the movement of the transducers relative to one another and the relative translational motions of the links. Every two links are connected by a pivot pin that allows rotation and translation of the links relative to each other. An angle sensor is mounted to at least one link proximate the pivot pin to allow for detection of the angle between the links. The ITML approach features less localizers than the individual transducer tracking design.

Figure 17:
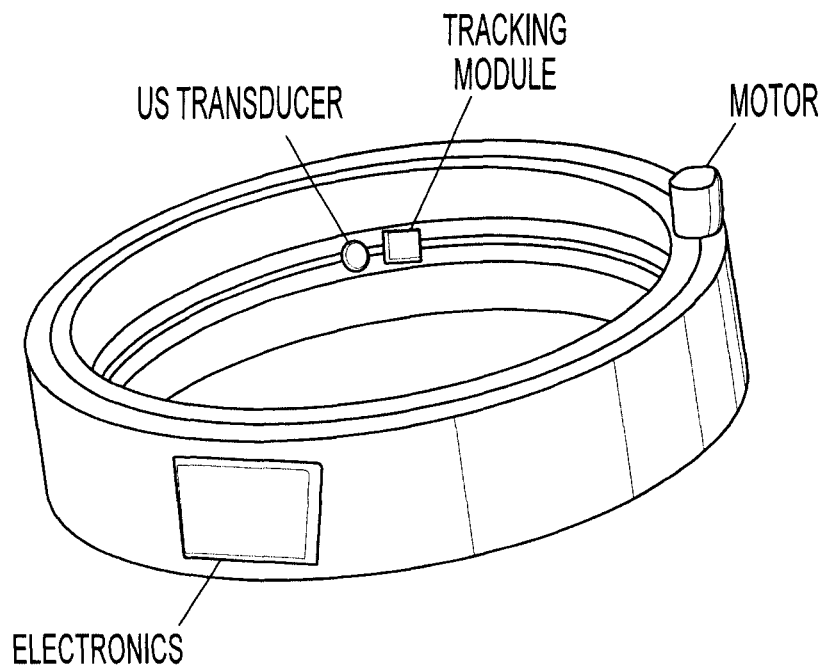
FIG. 17 is a pictorial representation of a further alternative kinematics exemplary tracking brace.

Referring to FIG. 17, a third approach, commonly referred to herein as the RT (Rotating Transducer) approach, involves using a single ultrasound transducer that is mounted to a carriage. The carriage traverses along a track located on the inner circumference of the brace. For example, the carriage may be moved along the tack by a string loop that is wrapped around the drive shaft of a motor. When the transducer reaches the motor, the rotation direction of the motor is changed and the transducer moves in the opposite direction.

An inertia-based localizer is mounted to the transducer to track its motion. As the transducer rotates within the inner circumference of the brace, it collects data as to the outer circumferential topography of the bone surface. By using a single transducer, the RT approach includes the advantage of lower cost than the stationary transducer designs and higher accuracy due to the greater number of localized bone surface points for each tracking step, while maintaining a mechanical flexibility.

Figure 18:
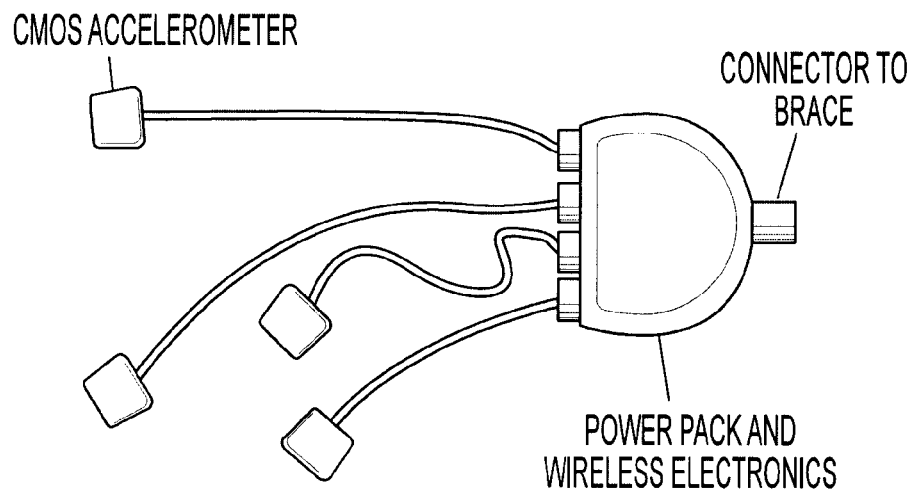
FIG. 18 is a pictorial representation of a vibration detection module.

Referring to FIG. 18 is the third module of the exemplary diagnostic system, the vibration detection module, includes thin film accelerometers that detect the vibration produced by motion of the knee joint. Thin film accelerometers are used in lieu of sound sensors, because of better performance and less noise susceptibility. In exemplary form, the thin film accelerometers may be the same ones used for the localizer, as well as having the same circuitry for driving the accelerometers. The accelerometers are attached to the patients and communicatively connected to the kinematic tracking braces so the outputs from the accelerometers can be amplified, digitized, and sent wirelessly to the controller computer.

Figure 22:
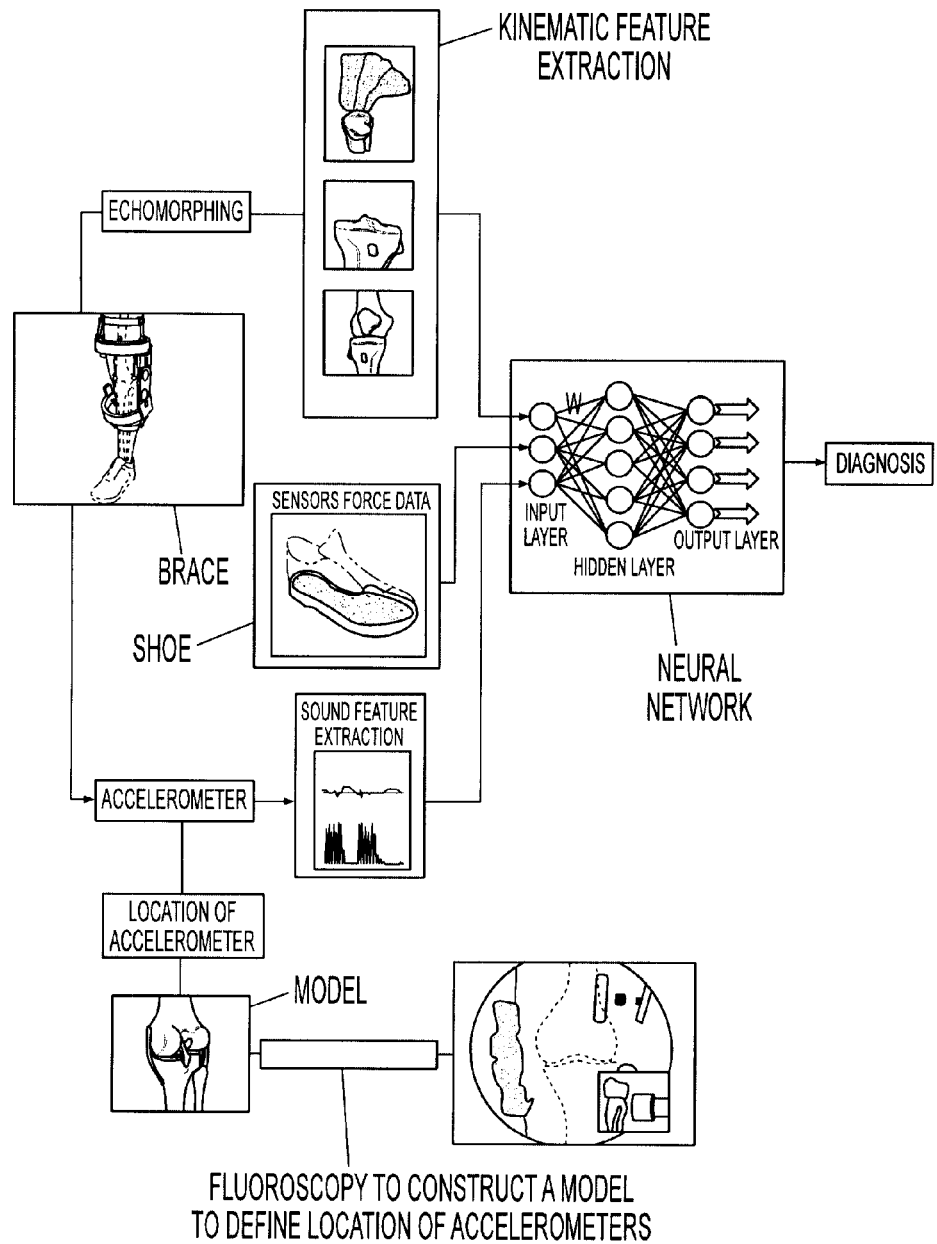
FIG. 22 is a is a schematic of the overall classification system flow chart.

Referring to FIG. 22, X-ray video fluoroscopy and in-vivo measurements of dynamic knee kinematics are important for understanding the effects of joint injuries, diseases, and evaluating the outcome of surgical procedures. In exemplary form, using the two aforementioned techniques, six degrees of freedom (DOF) are determined between the femur and tibia, femur and patella, and tibia and patella that involve the position and orientation of each with respect to the other. The accuracy of this approach is within one degree of rotation and one mm of translation (except for translation parallel to the viewing direction). Although this approach is highly accurate, it constrains the patient to remain within the small working volume of the fluoroscope unit and subjects the patient to ionizing radiation for a prolonged period of time. For most dynamic activities where the joints are loaded such as running, jumping, or other dynamic activities, fluoroscopy is an unacceptable alternative. To address this deficiency in preexisting approaches, an exemplary system accurately measures joint motion during dynamic activities using a portable brace, such as those previously discussed herein. By using a portable brace having sensors mounted thereto, X-ray fluoroscopy may be omitted.

Implementation of joint movement visualization includes using the exemplary 3C model reconstruction using pulse-echo A-mode ultrasound system to measure vibrations produced to accurately localize the exact vibration center and causes for its occurrence. The interpretation of the vibration and kinematic data is a complicated task involving an in-depth understanding of data acquisition, training data sets and signal analysis, as well as the mechanical system characteristics. Vibrations generated through the implant components, bones, and/or soft tissues interaction result from a forced vibration induced by driving force leading to a dynamic response. The driving force can be associated with the impact following knee ligament instability, bone properties, and conditions. A normal, intact knee will have a distinct pattern of motion, coupled with distinct vibrational characteristics. Once degeneration or damage occurs to the knee joint, both the kinematic patterns and vibrational characteristics become altered. This altering, for each type of injury or degeneration, leads to distinct changes that can be captured using both kinematic and vibration determination.

Figure 25:
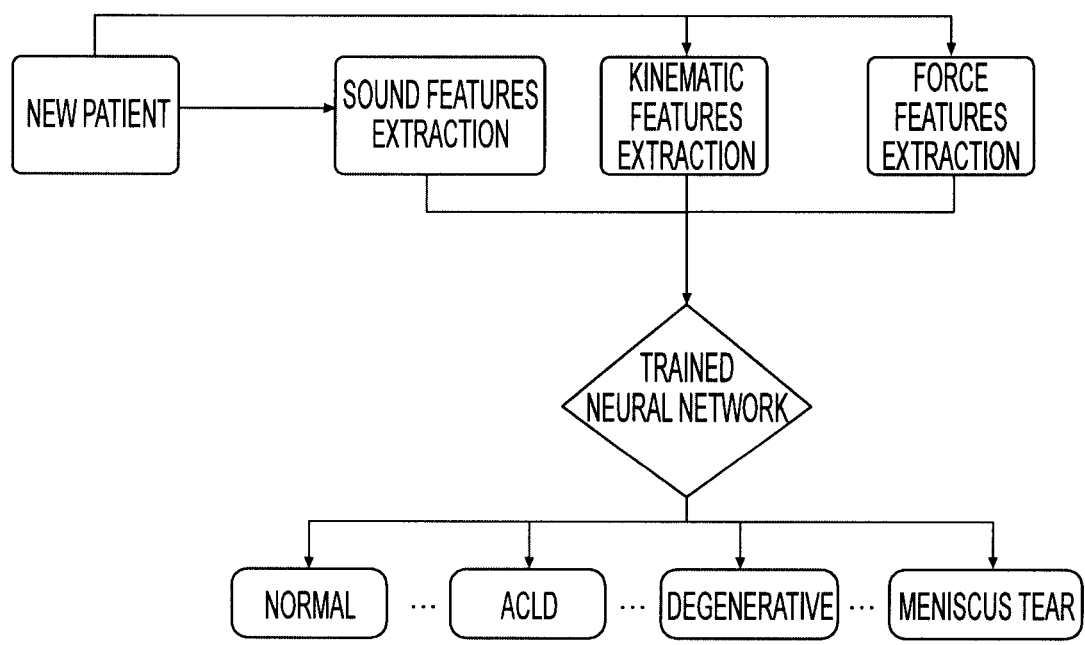
FIG. 25 is an exemplary process flow for knee deficiency diagnosis using a trained neural network.

Referencing FIG. 25, a fourth module of the exemplary diagnostic system, the intelligent diagnosis module, (This will be a software module) is operative to diagnose ligament, other soft tissue, and bone injuries. From previous studies, normal and anterior cruciate ligament deficient (ACLD) knee subjects exhibit a similar pattern of posterior femoral translation during progressive knee flexion, but the subjects exhibit different axial rotation patterns of 30 degrees of knee flexion. Accordingly, the diagnostic module is a two stage device that includes a first stage involving motion measurement extraction, while a second stage classifies any injury that is detected.

Figure 20:
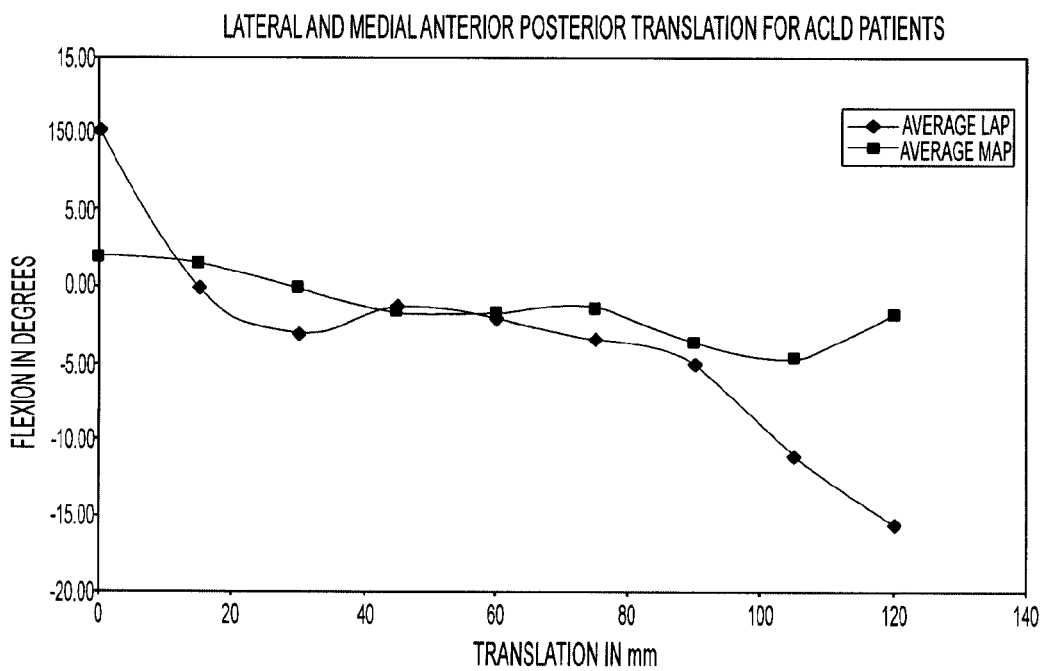
FIG. 20 is a graphical representation showing average ACLD medial and lateral condyle contact positions during a deep knee bend activity.
Figure 19A:
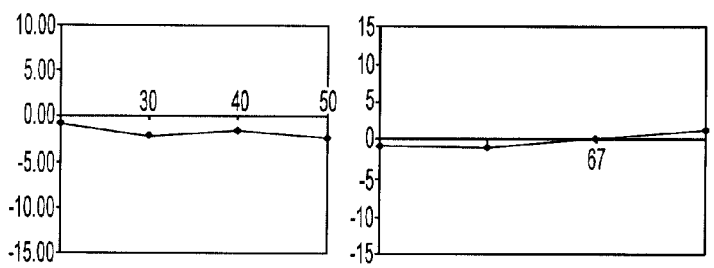
FIGS. 19A, 19B, and 19C are pictorial representations of exemplary kinematics data, vibration signal, and force data respectively.
Figure 19B:
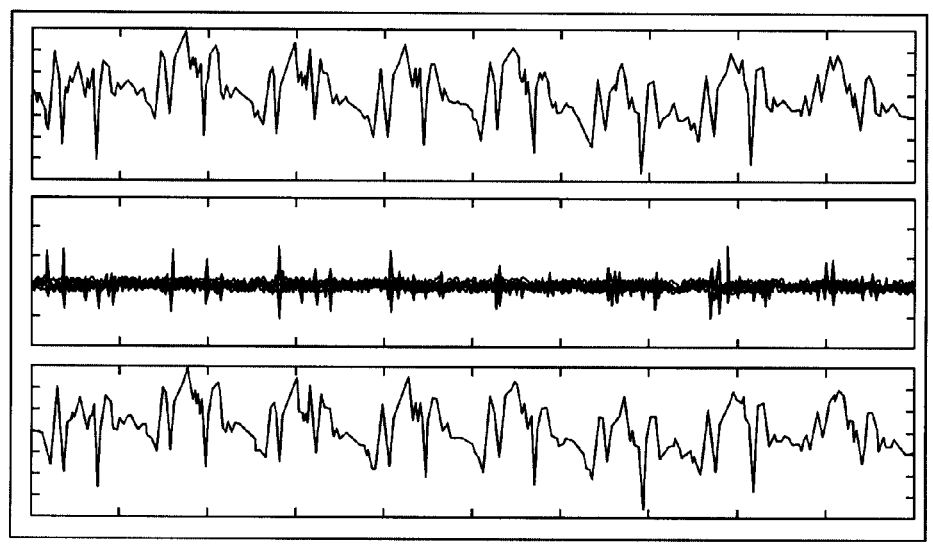
Figure 19C:
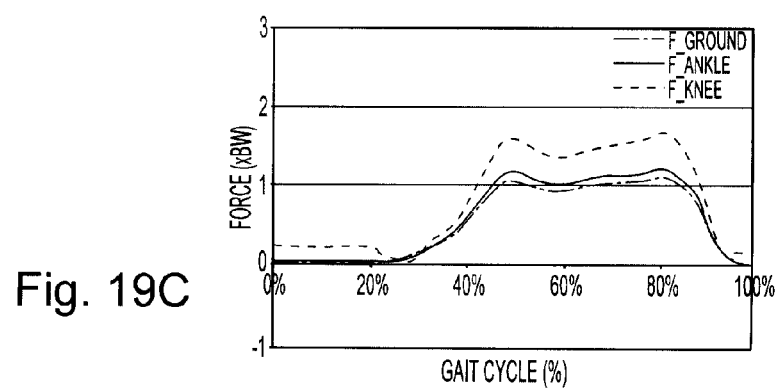
Figure 21A:
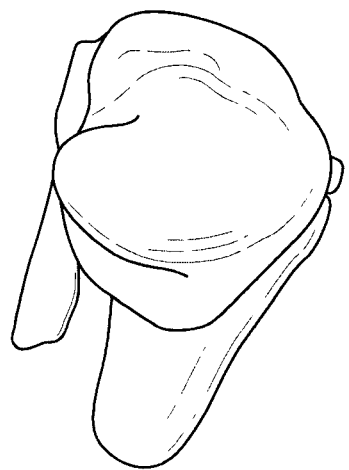
FIGS. 21A, 21B, and 21C are a series of views showing contact path tracking in accordance with the exemplary embodiments.
Figure 21B:
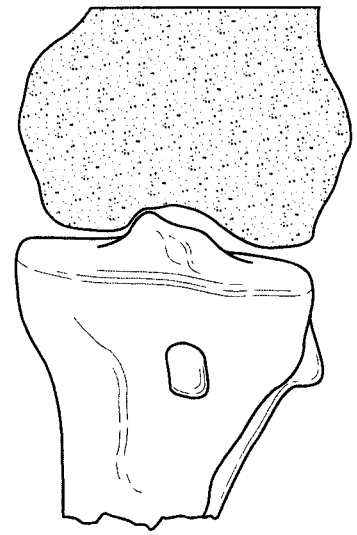
Figure 21C:
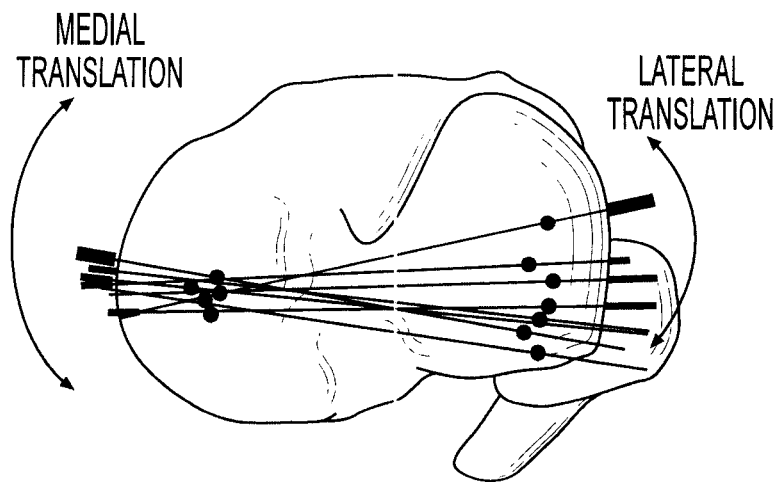

This first stage includes acquisition of kinematic feature vectors using multiple physiological measurements taken from the patient while the patient moves the joint in question through a range of motion. Exemplary measurements include, without limitation, medical condyle anteroposterior motion (MAP) and lateral condyle anteroposterior (LAP), with the latter pertaining to the anterior-posterior A/P distance of the medial and lateral condyle points relative to the tibia geometric center. Other exemplary measurements include LSI (distance between the lateral femoral condyle and the lateral tibial plateau) and MSI (distance between the medial femoral condyle and the medial tibial plateau) which are S/I (superior/inferior) distance of the lateral and medial condyle points to the tibial plane. Further exemplary measurements include condyle separation, which is the horizontal (x-y plane) distance between the two minimum condyle points to the tibia (See FIG. 21). Feature vectors also include the femoral position with respect to the tibia which is defined by three Euler angles and three translation components in addition to the vibration signal, and force data (see FIGS. 19A, 19B, and 19C). FIG. 20 is an exemplary graphical representation showing average ACLD medial and lateral condyle contact positions during a deep knee bend activity.

Referring to FIG. 22, the motion features vectors extracted from the kinematic and vibration analyses are output to a multilayer back propagation neural network for determining the injured ligament.

Figure 23:
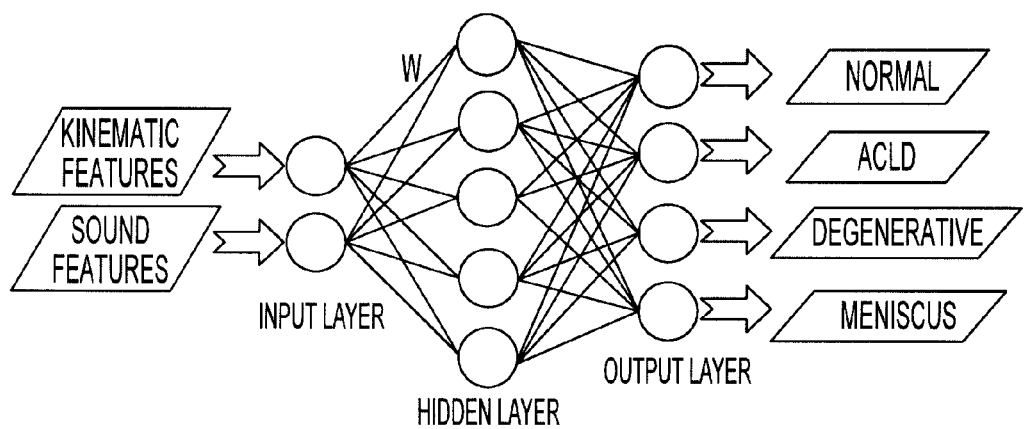
FIG. 23 is a schematic representation of an exemplary neural network classifier.

Referencing FIG. 23, an exemplary neural network classifier has multiple binary outputs. Each output is either a one or zero, with one corresponding to yeas and zero corresponding to no. In this exemplary neural network classifier, each output represents the response of the neural network to a particular injury type; for example one output will represent the response for anterior cruciate ligament deficiency (ACLD), its state will be one if an ACL injury is detected, and zero otherwise. Obviously, the neural network may be significantly more sophisticated or less sophisticated, depending upon the underlying model of the joint in question.

Figure 24:
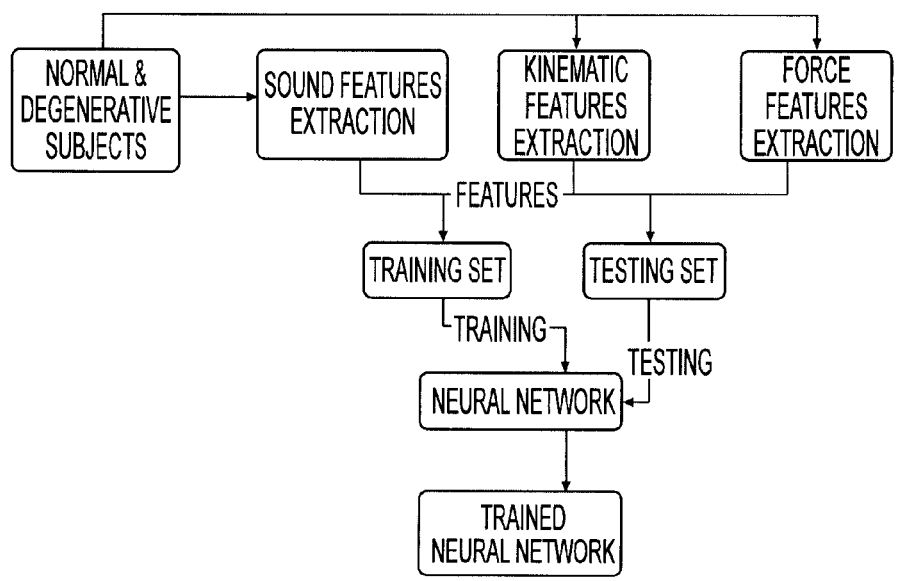
FIG. 24 is an exemplary process flow for training an exemplary neural network.

Referring to FIG. 24, construction of the exemplary neural network includes formulating a supervised classifier using a training set of the kinematic and vibration data corresponding to normal and injured knee joist. The NN is trained with a set of vectors. Each vector consists of data (kinematics, vibrations and forces) collected from one joint. Fluoroscopy data can be used to calculate the kinematics. Once the NN is trained, it can be used to classify new cases and categorize the injury type using these kinematics, vibration and forces data. Those skilled in the art will readily understand that the types and classifications desired to be accommodated by the neural network necessarily include training the neural network on these very types and classifications. Exemplary types and classifications of injuries to a mammalian knee joint include, without limitation, osteoarthritic conditions, soft tissue damage, and abnormal growths. Likewise, the neural network also needs to be trained as to indicators of normal knee function. In this manner, once the neural network is trained, it has the capability to differentiate between and output diagnosis data concerning normal and abnormal knee conditions.

Referencing FIG. 25, the vibration and kinematics features of a person's knee joint are compiled and fed to the trained neural network. The trained neural network then diagnoses the condition of the patient's knee joint, identifying and degeneration by type and severity.

Exemplary embodiments may be adapted to collect data outside of a clinical setting. For example, an exemplary embodiment may be worn by a patient for an extended period of time while performing normal activities. For example, a patient may wear vibration sensors and/or a kinematics tracking brace during activities that are not reproducible in the office (for example, weight lifting, racquet ball etc.) that elicit the pain or symptom. In some embodiments, the patient may turn the device on immediately prior to the activity and/or the patient may mark the event when it occurs. This enables analysis of the data just a few seconds before the marked time to see what abnormal sounds or joint kinematic were occurring. Data may be stored on a portable hard drive (or any other portable storage device) and then may be downloaded to exemplary systems for analysis. The data can be transmitted and stored in a computer wirelessly. It can also be stored with a miniature memory drive if field data is desired. If the occurrence of the pain was more random, exemplary devices allow continuous gathering of data. In embodiments, the patient may mark the event. Devices capable of continuous monitoring may require a larger data storage capacity.

It is also understood that while the exemplary embodiments have been described herein with respect to a knee joint, those skilled in the art will readily understand that the aforementioned embodiments may be easily adapted to other joints of a mammalian animal. For example, embodiments may be adapted for use on hips, ankles, toes, spines, shoulders, elbows, wrists, fingers, and temporomandibular joints.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that that any limitations or elements describing the exemplary embodiments set forth herein are to be incorporated into the interpretation of any claim element unless such claim limitation is explicitly stated. Likewise, it is to be understood that it is not necessary to meet any or all of the identified advantages or objects of the invention disclosed herein in order to fall within the scope of any claims. Since the invention is defined by the claims and since inherent and/or unforeseen advantages of the present invention may exist even though they any not have been explicitly discussed herein.

What is claimed is:

1. A method of tracking motion of an actual patient bone using creating a patient specific bone model, the method comprising:
   acquiring A-mode pulse echo ultrasound signals of the actual patient bone;
   utilizing the ultrasound signals to capture a point cloud representative of the actual patient bone;
   fitting a deformable 3-D bone model to the captured point cloud to generate a 3-D patient specific bone model;
   registering the actual patient bone with the 3-D patient specific bone model;
   generating at least one localized bone point from an output of one or more ultrasound transducers positioned proximate the actual patient bone;
   tracking the at least one localized bone point by tracking the motion of the one or more ultrasound transducers using one or more inertial sensors; and
   tracking motion of the actual patient bone through a range of motion using the at least one tracked localized bone point in combination with the 3-D patient specific bone model.

2. The method of claim 1 further comprising:
   displaying said motion on the 3-D patient specific bone model.

3. The method of claim 1, further comprising:
   selecting from a database a set of empirical mathematical descriptions of the motion of the actual patient bone through the range of motion; and
   comparing the motion of the actual patient bone to the selected set of empirical mathematical descriptions.

4. The method of claim 1, further comprising:
   collecting vibrational data as the actual patient bone is moved through the range of motion;
   selecting from a database a set of empirical vibrational data descriptions of the vibration of the actual patient bone through the range of motion; and
   comparing said vibrational data to the selected set of empirical vibration data descriptions.

5. The method of claim 1, further comprising:
   selecting one of a plurality of bone models;
   measuring the actual patient bone to obtain patient specific measurements; and
   applying the patient-specific measurements to the selected one of the plurality of bone models.

6. The method of claim 5, wherein selecting one of the plurality of bone models includes considering at least one demographic characteristic of the patient.

7. The method of claim 5, wherein applying the patient-specific measurements to the bone model includes conforming the model bone to the captured point cloud.

8. The method of claim 1, further comprising:
   placing an inertial sensor approximate the actual patient bone; and
   gathering vibration data using the inertial sensor while moving the actual patient bone through the range of motion.

9. The method of claim 8, further comprising:
   simultaneously, with gathering the vibration data, gathering kinematics data pertaining to the actual patient bone.

10. The method of claim 9, wherein the vibration data is time-synchronized with the kinematics data.

11. The method of claim 8, further comprising:
    analyzing the vibration data using a neural network.

12. The method of claim 11, further comprising:
    prior to analyzing the vibration data, training the neural network.

13. The method of claim 11, wherein analyzing the vibration data using the neural network further comprises:
    diagnosing at least one of a presence and severity of a joint condition.

14. The method of claim 13, wherein the step of analyzing the vibration data using a neural network further comprises:
    transmitting the vibration data across a network; and
    receiving data pertaining to the joint condition via the network.

15. The method of claim 1 wherein the patient is a mammalian animal.

* * * * *